(12) United States Patent
Yamada et al.

(10) Patent No.: US 10,703,696 B2
(45) Date of Patent: Jul. 7, 2020

(54) METHOD FOR ISOMERIZING ORGANIC COMPOUND, AND METHOD FOR PRODUCING ISOMER OF ORGANIC COMPOUND

(71) Applicant: AGC Inc., Chiyoda-ku (JP)

(72) Inventors: Taku Yamada, Chiyoda-ku (JP); Yusuke Suzuki, Chiyoda-ku (JP); Mitsugu Kasagawa, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 16/389,398

(22) Filed: Apr. 19, 2019

(65) Prior Publication Data

US 2019/0241490 A1 Aug. 8, 2019

Related U.S. Application Data

(63) Continuation of application No. PCT/JP2017/038957, filed on Oct. 27, 2017.

(30) Foreign Application Priority Data

Nov. 1, 2016 (JP) ................... 2016-214247

(51) Int. Cl.
*C07C 17/358* (2006.01)
*C07C 19/10* (2006.01)
(Continued)

(52) U.S. Cl.
CPC ........... *C07C 17/358* (2013.01); *B01J 27/125* (2013.01); *C07B 61/00* (2013.01); *C07B 2200/09* (2013.01)

(58) Field of Classification Search
CPC .................................................... C07C 17/358
See application file for complete search history.

(56) References Cited

U.S. PATENT DOCUMENTS 5,157,171 A 10/1992 Sievert et al.
2012/0004474 A1* 1/2012 Okamoto ................ C07C 17/25
570/151

FOREIGN PATENT DOCUMENTS

JP 2-108639 4/1990
JP 7-241474 9/1995
(Continued)

OTHER PUBLICATIONS

Molbase (Aluminum oxide, CAS 1344-28-1, pp. 1-26), Okamoto's alumina (ACBM-1).*
(Continued)

*Primary Examiner* — Medhanit W Bahta
(74) *Attorney, Agent, or Firm* — Oblon, McClelland, Maier & Neustadt, L.L.P.

(57) ABSTRACT

The method for isomerizing an organic compound comprises a step of selecting an alumina so that the acid amount calculated from the amount of ammonia desorbed at a desorption temperature of at least 300° C. by temperature-programmed desorption of ammonia is at least 0.10 mmol/g and at most 0.25 mmol/g; a step of fluorinating the selected alumina by a fluorinating agent to produce a partially fluorinated alumina; and a step of isomerizing, by using the obtained partially fluorinated alumina, an organic compound having at least two carbon atoms wherein to at least one of the adjacent carbon atoms, at least one fluorine atom is bonded and to the other, at least one chlorine atom or hydrogen atom is bonded.

19 Claims, 1 Drawing Sheet

(51) Int. Cl.
   *B01J 27/125*   (2006.01)
   *C07B 61/00*   (2006.01)

(56)      References Cited

FOREIGN PATENT DOCUMENTS

JP          2570829 B2    1/1997
   JP    WO2010/082662       7/2010
   JP          5598333 B2   10/2014

OTHER PUBLICATIONS

Santa Cruz Biotechnology (Aluminum oxide, gamma phase (CAS 1344-28-1), p. 1).*
International Search Report dated Dec. 12, 2017 in PCT/JP2017/038957 filed Oct. 27, 2017 (with English Translation).
T. Tanuma, et al., "Metal halide catalysts to synthesize dichloropentafluoropropanes by the reaction of dichlorofluoromethane with tetrafluoroethylene", Applied Catalysis A: General 348, 2008, 6 pages.

* cited by examiner

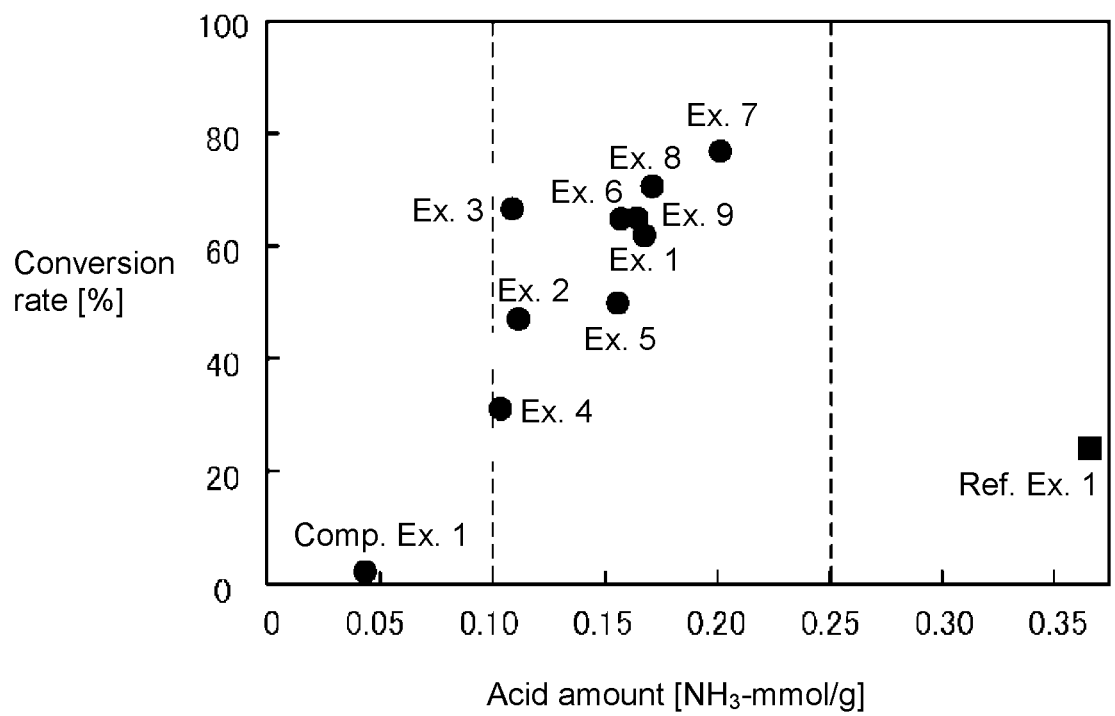

METHOD FOR ISOMERIZING ORGANIC COMPOUND, AND METHOD FOR PRODUCING ISOMER OF ORGANIC COMPOUND

TECHNICAL FIELD

The present invention relates to a method for isomerizing an organic compound having halogen atoms, in particular, to a method for isomerizing an organic compound, by using, as a catalyst, a fluorinated alumina obtainable by fluorination treatment after selecting an alumina having a predetermined property.

BACKGROUND ART

Heretofore, various methods have been proposed as methods for producing dichloropentafluoropropanes (HCFC-225) represented by chemical formula: $C_3HCl_2F_5$. For example, a method for obtaining dichloropentafluoropropanes by contacting dichlorofluoromethane with tetrafluoroethylene in the presence of a modified aluminum chloride catalyst has been proposed, and technology for applying isomerization to various isomeric mixtures of dichloropentafluoropropanes obtained by this method, has been disclosed (see e.g. Patent Document 1, Non-Patent Document 1).

Among the dichloropentafluoropropanes (HCFC-225), attention by the present applicant is paid to HCFC-225ca which can be a starting material for synthesizing 2,3,3,3-tetrafluoropropene ($CF_3CF=CH_2$; HFO-1234yf). That is, in recent years, it is considered to use HFO-1234yf or the like having a small ozone depletion potential, as a refrigerant, and usefulness of HCFC-225ca is being increased as a starting material to obtain 1,1-dichloro-2,3,3,3-tetrafluoropropene ($CF_3CF=CCl_2$; CFO-1214ya) as raw material for HFO-1234yf.

Under such circumstances, a method for efficiently obtaining HCFC-225ca has been found wherein, in order to efficiently obtain HCFC-225ca, a predetermined raw material is subjected to an isomerization reaction by partially fluorinated alumina (see Patent Document 2).

Further, in order to obtain a desired compound not limited to the above compound, various methods for isomerization by transposing substituents are known by using, as raw material, an organic compound containing chlorine atoms or fluorine atoms. As a catalyst for the isomerization reaction in such a case, a fluorinated alumina obtained by partially fluorinating an alumina, is known to be useful (see e.g. Patent Documents 3 and 4).

PRIOR ART DOCUMENTS

Patent Documents

Patent Document 1: U.S. Pat. No. 51,557,171
Patent Document 2: Japanese Patent No. 5598333
Patent Document 3: JP-A-H02-108639
Patent Document 4: JP-A-H07-241474

Non-Patent Document

Non-Patent Document 1: Applied Catalysis A: General, 348, p 236-240 (2008)

DISCLOSURE OF INVENTION

Technical Problems

With respect to the catalyst for the isomerization reaction, in order to obtain a compound having good catalytic activities, the composition after the fluorination, the physical properties such as the specific surface area, pore volume, etc. of the alumina to be catalyst raw material before the fluorination, etc., have been studied. Based on such composition, physical properties, etc., there are some guidelines for obtaining a fluorinated alumina having a certain degree of catalytic activities, but a method for judging what type of fluorinated alumina has catalytic activities has not yet been established, and in order to obtain a fluorinated alumina having good catalytic activities, it has been obliged to rely on trial and error by studying various fluorinated alumina.

Therefore, it is an object of the present invention to find out a useful evaluation method in order to efficiently obtain a partially fluorinated alumina with good catalytic activities, and to provide, by applying the evaluation method, a method for isomerization of an organic compound with a high conversion rate in the desired isomerization reaction and a method for producing an isomer of the organic compound.

Solution to Problems

The method for isomerizing an organic compound of the present invention is characterized by comprising a step of selecting an alumina, so that the acid amount calculated from the amount of ammonia desorbed at a desorption temperature of at least 300° C. by temperature programmed desorption of ammonia is at least 0.10 mmol/g and at most 0.25 mmol/g, a step of fluorinating the selected alumina by a fluorinating agent to obtain a partially fluorinated alumina, and a step of isomerizing, by using the obtained partially fluorinated alumina, an organic compound having at least two carbon atoms, wherein to at least one of the adjacent carbon atoms, at least one fluorine atom is bonded and to the other, at least one chlorine atom and/or hydrogen atom is bonded.

Further, the method for producing an isomer of an organic compound of the present invention, is characterized by producing, by the above method for isomerizing an organic compound, an isomer of the organic compound, wherein a fluorine atom in said organic compound is rearranged.

Advantageous Effects of Invention

According to the method for isomerizing an organic compound of the present invention, it is possible to efficiently obtain a partially fluorinated alumina with good catalytic activities, and by using this partially fluorinated alumina as a catalyst for the isomerization reaction, it is possible to perform the isomerization reaction with a good conversion rate without relying on trial and error. By using this isomerization method, it is possible to efficiently obtain an isomer of an organic compound.

By efficiently obtaining a partially fluorinated alumina with good catalytic activities, it is possible to carry out the isomerization reaction in a temperature range where it is possible to suppress side reactions, and it is possible to efficiently obtain the desired isomer of an organic compound in good yield.

By using the isomerization method of the present invention, it is possible to efficiently produce the desired organic compound, and it is possible to reduce the production cost.

BRIEF DESCRIPTION OF DRAWING

FIGURE is a graph showing the relationship between the acid amount of the alumina and the conversion rate for the isomerized organic compound.

DESCRIPTION OF EMBODIMENT

The method for isomerizing an organic compound, and the method for producing an isomer of an organic compound, according to the present invention, will be described below with reference to an embodiment.

The method for isomerizing an organic compound in the present embodiment comprises a step of selecting an alumina, a step of fluorinating the alumina to obtain a partially fluorinated alumina, and a step of isomerizing, by using the obtained partially fluorinated alumina, a predetermined organic compound containing fluorine atoms. In the following, the respective steps constituting the present embodiment will be described in detail.

[Method for Isomerizing Organic Compound]
(Step of Selecting Alumina)

In the step of selecting an alumina, an alumina which becomes raw material for the partially fluorinated alumina as described later, is selected. The partially fluorinated alumina will be used as a catalyst for the isomerization reaction, in the step of isomerizing an organic compound as described later. Here, by selecting an alumina having a predetermined property, it is possible to obtain a partially fluorinated alumina with good catalytic activities for the isomerization reaction in the treatment as described later.

The alumina to be selected here, is one, of which the acid amount calculated from the amount of ammonia desorbed at a desorption temperature of at least 300° C. by temperature programmed desorption of ammonia is at least 0.10 mmol/g and at most 0.25 mmol/g, preferably at least 0.15 mmol/g and at most 0.25 mmol/g. By adjusting this acid amount to be at least 0.10 mmol/g, it becomes easy to prepare a partially fluorinated alumina with a good conversion rate in the isomerization reaction as described below, and by adjusting it to be at most 0.25 mmol/g, it is possible to suppress the reaction temperature and suppress side reactions to improve the yield of the desired isomer of an organic compound. When it is at least 0.15 mmol/g and at most 0.25 mmol/g, it will be particularly easy to prepare the partially fluorinated alumina, and it is possible to suppress side reactions to improve the yield of the isomer.

Here, temperature programmed desorption of ammonia ($NH_3$-TPD) is a method wherein after letting ammonia ($NH_3$) be adsorbed to a test sample, the temperature is raised at a constant rate, and the amount of ammonia desorbed at that time is measured to obtain the interrelation of the desorbed amount of ammonia to the temperature, thereby to evaluate the acid amount of the test sample from the desorbed amount and the acid strength from the desorption temperature.

In this method, the desorption temperature of ammonia varies depending on the form in which ammonia is adsorbed at the alumina surface. That is, at the alumina surface, ammonia adsorbed to active sites with a low acid strength will be desorbed at a low temperature side, and ammonia adsorbed to active sites with a high acid strength will be desorbed at a high temperature side. Therefore, by measuring and analyzing the desorbed amount of ammonia at the low temperature side and the desorbed amount of ammonia at the high temperature side, respectively, it is possible to judge the characteristics of the test sample.

This temperature programmed desorption of ammonia is carried out, for example, by heating from room temperature to about 1,000° C. continuously at a temperature raising rate of from 1° C./min. to 20° C./min., whereby the desorbed amount of ammonia and the desorption temperature are measured.

In an alumina, there are two peaks in the desorbed amount of ammonia, i.e. the first peak which appears in the vicinity of 200° C. and the second peak which appears at a temperature of at least 300° C. Here, the first peak represents the desorption from the above-mentioned active sites with a low acid strength, and the second peak represents the desorption from the above-mentioned active sites with a high acid strength, and in this specification, the desorbed amount of ammonia represented by the second peak is taken as the acid amount, as it is, and it is evaluated as the catalytic activities. It is considered that the higher the acid amount, the higher the catalytic performance in the isomerization reaction, of the partially fluorinated alumina obtained by the fluorination as described later.

Here, in practice, the desorbed amounts at the low temperature side and at the high temperature side are measured as partially overlapped, and otherwise, there are variations in the measured values also due to the influence of e.g. water, solvent, etc. Therefore, the desorbed amounts of ammonia at the low temperature side and at the high temperature side will be calculated by analyzing the obtainable graph by a predetermined analysis software, and based on these values (the desorbed amounts of ammonia), the acid amount will be determined.

The desorbed amounts of ammonia can be calculated by the temperature programmed desorption of ammonia as described below.

This temperature programmed desorption of ammonia can be conducted, for example, as follows, by using a catalyst analyzer (manufactured by MicrotracBEL Corp., BELCAT II) as the analyzer, He (helium) as the carrier gas, and TCD (thermal conductivity detector) as the detector.

(Pre-Treatment)

First, γ-alumina precisely weighed in an amount of 0.10 g in a TPD measurement cell was, under a flow of helium at 50 mL/min., heated to 500° C. at a rate of 10° C./min. and held at 500° C. for 1 hour for dehydration.

($NH_3$ Treatment)

The γ-alumina after the dehydration was cooled to 100° C. and held for 30 minutes under a flow of 0.5% $NH_3$/He at 100 mL/min., to adsorb $NH_3$.

(Post Treatment)

The γ-alumina after the $NH_3$ adsorption treatment was held at 100° C. for 30 minutes, under a flow of helium at 50 mL/min., to desorb $NH_3$ physically adsorbed in the TPD measurement cell.

(TPD Measurement)

The pretreated γ-alumina was, under a flow of helium at 100° C. at 50 mL/min., heated to 810° C. at a temperature raising rate of 10° C./min.

The amount at acid sites is determined as an amount relative to the high peak (the peak at the high temperature side among the two types of observed peaks) of ZSM-5 type zeolite (manufactured by ExxonMobil Catalyst Co., Ltd., product name: JRC-Z5-25H) being 0.99 mmol/g.

(Analysis Method)

In the present embodiment, taking the desorbed amount of ammonia in a temperature range of from the start of measurement to a desorption temperature of 300° C. as the weak acid amount and the desorbed amount of ammonia at a desorption temperature of at least 300° C. as the strong acid amount, from the obtained data, the respective peaks are waveform-separated by a non-linear least-squares method, on the assumption that they follow a normal distribution, whereupon the respective desorbed amounts of ammonia are calculated to determine the acid amounts.

Alumina has various types depending on its crystal structure, but the alumina used here as raw material is an alumina having a high catalytic activities so-called activated alumina, and in this specification, is an acidic activated alumina satisfying the above-mentioned acid amount. The crystal form of this activated alumina is not particularly limited, but generally, γ-alumina, η-alumina, etc. with good activities may be mentioned as preferred ones, and among them, γ-alumina being an alumina having a γ-$Al_2O_3$ structure is more preferred.

With respect to the crystal structure, by a diffraction pattern measured by XRD (X-Ray Diffractometer, manufactured by Rigaku Corporation, product name: SmartLab), the main product may be identified as γ-alumina from the diffraction peak of d=1.40, 1.99, 2.4 Å.

Further, the specific surface area and pore volume of the alumina may be measured by a nitrogen adsorption method by means of 3Flex manufactured by Micromeritics Instrument Corporation.

(Step of Obtaining Partially Fluorinated Alumina)

The step of obtaining a partially fluorinated alumina in the present embodiment is a step of contacting and reacting the alumina having the predetermined property selected in the above step, with a fluorinating agent, to partially fluorinate it. Here, the fluorination can be carried out, for example, by contacting the alumina as raw material with a fluorinating agent in a gas phase at a high temperatures, to bond a fluorine atom to the aluminum atom of the alumina. Otherwise, by other known fluorination treatments, the alumina may be made to be the fluorinated alumina.

The fluorinating agent to be used here is not particularly limited as long as it is a compound having a fluorine source capable of fluorinating the alumina, and, for example, an inorganic compound containing fluorine atom(s), such as hydrogen fluoride (HF), $SF_4$, $SOF_2$, $COF_2$, etc. may be mentioned, or a carbon compound having a substituent containing fluorine atom(s) may be mentioned. The carbon compound having a substituent containing fluorine atom(s) may, for example, be a fluorocarbon such as a chlorofluorocarbon, a hydrochlorofluorocarbon, a hydrofluorocarbon, etc.

Here, as the fluorinating agent, one capable of fluorinating the alumina may be used, and the organic compound to be isomerized as described in the next step may be used. That is, in such a case, the fluorinating agent and the raw material compound for the isomerization will be the same, and thus, it is possible to reduce the types of raw materials to be used (there will be no need to prepare a fluorinating agent separately), and along therewith, the structure of the device, etc. can be simplified, whereby the implementation cost for the isomerization method can be reduced.

From such a viewpoint that precipitation of coke can be reduced, the fluorinating agent is preferably hydrogen fluoride or a $C_{1-3}$ carbon compound having a substituent containing fluorine atom(s), more preferably an organic compound having at least two carbon atoms. In the case of not using the organic compound to be isomerized as described in the next step, the fluorinating agent is preferably a fluorine compound different from the above-mentioned organic compound having at least two carbon atoms, or hydrogen fluoride.

(Step of Isomerizing Organic Compound)

The step of isomerizing an organic compound containing fluorine in the present embodiment is one wherein as the organic compound to be isomerized, an organic compound having at least two carbon atoms, wherein to at least one of the adjacent carbon atoms, at least one fluorine atom is bonded and to the other, at least one chlorine atom and/or hydrogen atom is bonded, is used.

The organic compound to be used here is not particularly limited so long as it is an organic compound having the above structure, and, for example, a fluorocarbon such as a chlorofluorocarbon, a hydrochlorofluorocarbon or a hydrofluorocarbon may be mentioned.

The chlorofluorocarbon (CFC) may, for example, be trichlorotrifluoroethane (CFC-113), dichlorotetrafluoroethane (CFC-114), monochloropentafluoroethane (CFC-115), etc.

The hydrochlorofluorocarbon may, for example, be dichlorotrifluoroethane (HCFC-123), chlorotetrafluoroethane (HCFC-124), dichlorofluoroethane (HCFC-141), dichloropentafluoropropane (HCFC-225), etc.

The hydrofluorocarbon may, for example, be difluoroethane (HFC-152), trifluoroethane (HFC-143), tetrafluoroethane (HFC-134), pentafluoroethane (HFC-125), pentafluoropropane (HFC-245), hexafluoropropane (HFC-236), heptafluoropropane (HFC-227), pentafluorobutane (HFC-365), heptafluorocyclopentane (HFC-c447), etc.

As the organic compound, a hydrofluorochloropropane is preferred, and 1,3-dichloro-1,1,2,2,3-pentafluoropropane (HCFC-225cb) or 2,2-dichloro-1,1,1,3,3-pentafluoropropane (HCFC-225aa) may be mentioned as a particularly preferred one. When they are used alone or as a mixed raw material, the isomers of the organic compounds obtainable by isomerization are 3,3-dichloro-1,1,1,2,2-pentafluoropropane (HCFC-225ca). HCFC-225ca may be used as a starting material to obtain CFO-1214ya as raw material for synthesizing HFO-1234yf.

Such a predetermined organic compound is contacted with the partially fluorinated alumina obtained as described above, to isomerize the organic compound. At that time, in the organic compound, the bonding position of its fluorine atom to a carbon atom will be rearranged to e.g. the adjacent carbon atom. That is, the obtainable organic compound after the isomerization is one wherein the positions of the fluorine atom and the chlorine atom or hydrogen atom, are interchanged with the organic compound as raw material, so that they have a relationship of isomers of each other.

Further, since such reactions may occur in succession, there may be a case wherein a fluorine atom may be moved to a carbon atom apart by two or more positions from the carbon atom to which the fluorine atom was originally bonded.

In this isomerization reaction, it is preferred to carry out the isomerization by letting the organic compound as the raw material be in contact with the partially fluorinated alumina in a gas phase. This isomerization reaction can be carried out under heating at the reaction temperature of at least 150° C. and at most 500° C.

The suitable reaction temperature may vary depending on the raw material compound to be used, the type, ratio, etc. of the compound, etc., and therefore, the reaction conditions may be set so that the desired isomer of the organic compound will be obtained. In general, if the reaction temperature becomes high, a disproportionation reaction proceeds among isomeric compounds to form a by-product, and therefore, the reaction temperature in the present embodiment is preferably from 150 to 500° C., more preferably from 200 to 450° C. The raw material compound to be used is preferably a compound present as a gas without being decomposed at the reaction temperature. In the present embodiment, since a partially fluorinated alumina with good catalytic activities is used, it is possible to let the reaction proceed even by heating at a low temperature as described above.

[Method for Producing Isomer of Organic Compound]

Further, in the method for producing an isomer of an organic compound in the present embodiment, an isomer of an organic compound is produced by letting fluorine atom(s) in the raw material organic compound be rearranged (isomerized) by using the above-described method for isomerizing an organic compound.

This method for producing an isomer of an organic compound employs the above-described method for isomerizing an organic compound, and is one expressed from the product compound side, and thus, the substantive content is the same. Therefore, the content of this invention is already described by the foregoing description, and detailed description thereof will be omitted.

EXAMPLES

Hereinafter, the present invention will be specifically described with reference to Examples and Comparative Examples, but the present invention is by no means limited by such description.

Example 1

Boehmite was calcined to prepare $\gamma$-$Al_2O_3$ i.e. alumina with a specific surface area of 229 $m^2/g$ and a total pore volume of 0.69 mL/g (hereinafter referred to as alumina 1).

0.10 g of this alumina 1 was taken as a sample, and acid sites were measured by $NH_3$-TPD. From the obtained measurement data, on the assumption that the respective peaks of the weak acid point and strong acid point are to follow a normal distribution, waveforms are separated by a non-linear least-squares method to calculate the acid amounts. As a result, the desorption temperature (acid strength) at the strong acid point of alumina 1 was 321° C. and the acid amount was 0.132 mmol/g.

25 mL of this alumina 1 was weighed and packed in a reactor tube made of SUS-316 having an internal diameter of 1.09 cm and a length of 350 cm, and the reactor tube was set in a tubular electric furnace maintained at 250° C. to dehydrate the catalyst. Then, the temperature was raised to 400° C., and by circulating a 2/1 (mol/mol) mixed gas of nitrogen/HCFC-225cb in a contact time of 20 seconds, to flow for 4 hours while performing fluorination of the alumina catalyst, whereby the isomerization reaction to HCFC-225ca was carried out. The conversion rate was obtained by analyzing the gas taken out from the outlet of the reactor by gas chromatography and calculating from the area % in the obtained GC chart.

At that time, the conversion rate was calculated from the amount of HCFC-225cb contained after the isomerization treatment relative to the amount of HCFC-225cb contained in the raw material.

Here, as the raw material composition used in this Example, ASAHIKLIN AK-225G (HCFC-225cb, manufactured by Asahi Glass Co., Ltd.) was used.

Examples 2 to 9

In the same manner as in Example 1 except that the alumina used was changed to the alumina indicated below, the acid amount of the alumina was measured, then the partially fluorinated alumina was prepared, and by using this, the isomerization reaction of an organic compound was conducted. The alumina used was as follows. The physical properties thereof and the conversion rate in the isomerization reaction are summarized in Table 1 in the same manner as in Example 1.

Here, the alumina used was as follows.

Alumina 2: Product name SAS-200 (manufactured by BASF, specific surface area: 200 $m^2/g$, total pore volume: 0.50 mL/g)

Alumina 3: A catalyst having product name F-200 (manufactured by BASF) calcined at 600° C. for 10 hours in air atmosphere, to have a $\gamma$-$Al_2O_3$ structure (specific surface area: 184 $m^2/g$, total pore volume: 0.23 mL/g)

Alumina 4: A catalyst having product name Axsorb AB (manufactured by Nippon Light Metal Company, Ltd.) calcined at 600° C. for 10 hours in air atmosphere, to have a $\gamma$-$Al_2O_3$ structure (specific surface area: 177 $m^2/g$, total pore volume: 0.48 mL/g)

Alumina 5: $\gamma$-$Al_2O_3$ prepared by calcining boehmite (specific surface area: 178 $m^2/g$, total pore volume: 0.72 mL/g)

Alumina 6: $\gamma$-$Al_2O_3$ prepared by calcining boehmite (specific surface area: 180 $m^2/g$, total pore volume: 0.73 mL/g)

Alumina 7: $\gamma$-$Al_2O_3$ prepared by calcining boehmite (specific surface area: 172 $m^2/g$, total pore volume: 0.78 mL/g)

Alumina 8: $\gamma$-$Al_2O_3$ prepared by calcining boehmite (specific surface area: 188 $m^2/g$, total pore volume: 0.81 mL/g)

Alumina 9: $\gamma$-$Al_2O_3$ prepared by calcining boehmite (specific surface area: 175 $m^2/g$, total pore volume: 0.78 mL/g)

Comparative Example 1

The isomerization reaction of an organic compound was conducted in the same manner as in Example 1 except that the alumina used was changed to alumina C1: product name Selexsorb COS (manufactured by BASF, specific surface area: 150 $m^2/g$, total pore volume: 0.46 mL/g). The physical properties of the alumina used and the conversion rate in the isomerization reaction are shown in Table 1 in the same manner as in Example 1.

Reference Example 1

Zeolite: product name HSZ-330H (manufactured by Tosoh Corporation; specific surface area: 269 $m^2/g$, total pore volume: 0.18 mL/g) was used as the catalyst for the isomerization reaction, and by using it as it is, the isomerization reaction of an organic compound was carried out in the same manner as in Example 1. The physical properties of zeolite used and the conversion rate in the isomerization reaction are shown in Table 1 in the same manner as in Example 1.

TABLE 1

| | Catalyst | Specific surface area [m²/g] | Total pore volume [mL/g] | Acid amount (desorbed amount of ammonia) | | Conversion rate [%] |
| --- | --- | --- | --- | --- | --- | --- |
| | | | | Peak temperature [° C.] | Acid amount [mmol/g] | |
| Example 1 | Alumina 1 | 229 | 0.69 | 323 | 0.171 | 61 |
| Example 2 | Alumina 2 | 200 | 0.5 | 344 | 0.111 | 46 |
| Example 3 | Alumina 3 | 184 | 0.23 | 348 | 0.110 | 65 |
| Example 4 | Alumina 4 | 177 | 0.48 | 350 | 0.102 | 31 |
| Example 5 | Alumina 5 | 178 | 0.72 | 352 | 0.158 | 50 |
| Example 6 | Alumina 6 | 180 | 0.73 | 345 | 0.162 | 64 |
| Example 7 | Alumina 7 | 172 | 0.78 | 347 | 0.200 | 76 |
| Example 8 | Alumina 8 | 188 | 0.81 | 361 | 0.174 | 70 |
| Example 9 | Alumina 9 | 175 | 0.78 | 350 | 0.170 | 64 |
| Comparative Example 1 | Alumina C1 | 150 | 0.46 | 344 | 0.044 | 1 |
| Reference Example 1 | Zeolite | 269 | 0.18 | 347 | 0.315 | 17 |

[Specific surface area]: Measured by a nitrogen adsorption method by means of 3Flex manufactured by Micromeritics Instrument Corporation.

[Total pore volume]: Measured by a nitrogen adsorption method by means of 3Flex manufactured by Micromeritics Instrument Corporation.

[Acid amount (desorbed amount of ammonia): By means of a catalyst analyzer BEACT II (manufactured by Microtrac-BEL Corp., product name), the alumina used in each Example was heated from room temperature to 810° C. at a temperature-raising rate of 10° C./min., whereby the desorbed amount relative to the desorption temperature of ammonia was measured. From the obtained graph, the desorbed amount of ammonia at a desorption temperature of at least 300° C. was calculated, and this was adopted as the acid amount of the alumina.

[Conversion rate]: Calculation of the conversion rate was performed by the following formula.

From area % of the gas composition by a gas chromatography analysis, it was calculated by [the content of HCFC-225cb in raw material–the content of HCFC-225cb after isomerization treatment].

Further, the relationship between the acid amount (desorbed amount of ammonia) and the conversion rate in the isomerization reaction, of the alumina and zeolite used in the above Examples and Comparative Example, is shown in the FIGURE. From the FIGURE, it was found that there is such a tendency that by partially fluorinating an alumina having a high acid amount, a catalyst having a high conversion rate is obtainable.

According to the method for isomerizing an organic compound of the present invention, by selecting an alumina having the predetermined property, it is possible to obtain a partially fluorinated alumina with a high conversion rate. Thus, it is possible to carry out the isomerization reaction at a high conversion rate without relying on trial and error. By using this isomerization method, it is possible to efficiently obtain an isomer of an organic compound.

This application is a continuation of PCT Application No. PCT/JP2017/038957, filed on Oct. 27, 2017, which is based upon and claims the benefit of priority from Japanese Patent Application No. 2016-214247 filed on Nov. 1, 2016. The contents of those applications are incorporated herein by reference in their entireties.

What is claimed is:

1. A method for isomerizing a chlorofluorocarbon and/or a hydrofluorocarbon having at least two carbon atoms, comprising:
    selecting an alumina in which an acid amount calculated from an amount of ammonia desorbed at a desorption temperature of at least 300° C. is at least 0.10 mmol/g and at most 0.25 mmol/g,
    applying a fluorinating agent to the selected alumina to fluorinate the selected alumina and obtain a partially fluorinated alumina, and
    contacting the chlorofluorocarbon and/or the hydrofluorocarbon having at least two carbon atoms with the obtained partially fluorinated alumina to interchange a position of a fluorine atom and a position of a chlorine atom or a hydrogen atom in the chlorofluorocarbon and/or the hydrofluorocarbon to isomerize the chlorofluorocarbon and/or a hydrofluorocarbon, wherein in the chlorofluorocarbon and/or a hydrofluorocarbon, to at least one of adjacent carbon atoms, at least one fluorine atom is bonded and to the other of the adjacent carbon atoms, at least one of chlorine atom and hydrogen atom is bonded.

2. The method according to claim 1, wherein the fluorinating agent is an organic compound having at least two carbon atoms.

3. The method according to claim 1, wherein the fluorinating agent is a fluorine compound other than an organic compound having at least two carbon atoms, or hydrogen fluoride.

4. The method according to claim 1, wherein in a gas phase, the alumina is fluorinated by the fluorinating agent to obtain the partially fluorinated alumina.

5. The method according to claim 1, wherein the acid amount is at least 0.15 mmol/g and at most 0.25 mmol/g.

6. The method according to claim 1, wherein the organic compound is a hydrofluorochloropropane.

7. The method according to claim 6, wherein the hydrofluorochloropropane comprises 1,3-dichloro-1,1,2,2,3-pentafluoropropane, and by the isomerization, 3,3-dichloro-1,1,1,2,2-pentafluoropropane is obtained.

8. The method according to claim 1, wherein the acid amount is at least 0.102 mmol/g and at most 0.200 mmol/g.

9. The method for according to claim 1, wherein the alumina has a γ-$Al_2O_3$ structure.

10. The method according to claim 9, wherein in a gas phase, the alumina is fluorinated by the fluorinating agent to obtain the partially fluorinated alumina.

11. The method according to claim 10, wherein the acid amount is at least 0.15 mmol/g and at most 0.25 mmol/g.

12. The method according to claim 10, wherein the organic compound is a hydrofluorochloropropane.

13. The method according to claim 12, wherein the hydrofluorochloropropane comprises 1,3-dichloro-1,1,2,2,3-pentafluoropropane, and by the isomerization, 3,3-dichloro-1,1,1,2,2-pentafluoropropane is obtained.

14. The method according to claim 13, wherein the acid amount is at least 0.102 mmol/g and at most 0.200 mmol/g.

15. The method according to claim 10, wherein the acid amount is at least 0.102 mmol/g and at most 0.200 mmol/g.

16. The method according to claim 9, wherein the acid amount is at least 0.15 mmol/g and at most 0.25 mmol/g.

17. The method according to claim 9, wherein the organic compound is a hydrofluorochloropropane.

18. The method according to claim 17, wherein the hydrofluorochloropropane comprises 1,3-dichloro-1,1,2,2,3-pentafluoropropane, and by the isomerization, 3,3-dichloro-1, 1,1,2,2-pentafluoropropane is obtained.

19. The method according to claim 9, wherein the acid amount is at least 0.102 mmol/g and at most 0.200 mmol/g.

\* \* \* \* \*